(12) United States Patent
Hendler

(10) Patent No.: US 6,362,234 B1
(45) Date of Patent: Mar. 26, 2002

(54) WATER-SOLUBLE PRODRUGS OF PROPOFOL FOR TREATMENT OF MIGRANE

(75) Inventor: Sheldon S. Hendler, La Jolla, CA (US)

(73) Assignee: Vyrex Corporation, La Jolla, CA (US)

( * ) Notice: Subject to any disclaimer, the term of this patent is extended or adjusted under 35 U.S.C. 154(b) by 0 days.

(21) Appl. No.: 09/639,015

(22) Filed: Aug. 15, 2000

(51) Int. Cl.$^7$ .................. A61K 31/05; A61K 31/405; A61K 31/19; A61K 31/16
(52) U.S. Cl. .................. 514/731; 514/415; 514/569; 514/570; 514/629
(58) Field of Search .................. 514/731, 415, 514/569, 570, 629

(56) References Cited

U.S. PATENT DOCUMENTS

| | | | | |
|---|---|---|---|---|
| 5,767,117 A | * | 6/1998 | Moskowitz | 514/219 |
| 5,891,875 A | * | 4/1999 | Hipskind et al. | 514/235.2 |
| 6,204,257 B1 | * | 3/2001 | Stella et al. | 514/130 |
| 6,254,853 B1 | * | 7/2001 | Hendler et al. | 424/45 |

FOREIGN PATENT DOCUMENTS

| | | | |
|---|---|---|---|
| WO | WO 99/58555 | 11/1999 | C07K/9/00 |

OTHER PUBLICATIONS

"Water–Soluble Salts of Aminoacid Esters of the Anaesthetic Agent Propofol", Trapani et al., 1998, International Journal of Pharmaceutics, 175, 195–204.*

"Propofol Analogues, Synthesis, Relationship between Structure and Affinity at GABAa Receptor in Rat Brain, and Differential Electrophysiological Profile at Recombinant Human Gabaa Receptors", Trapani et al, J Med. Chemistry, 41:1846–54 (1998).*

Krusz, et al., "Intravenous propofol: Unique effectiveness in treating intractable migraine," *Headache*, 40:224–230 (2000).

* cited by examiner

*Primary Examiner*—Zohreh Fay
*Assistant Examiner*—Brian-Yong Kwon
(74) *Attorney, Agent, or Firm*—Townsend and Townsend and Crew LLP

(57) ABSTRACT

This invention provides esters of propofol (2,6-diisopropylphenol). The propofol esters are soluble in water and metabolize rapidly to propofol in the body. The propofol esters are useful as prodrugs for the same indications as propofol.

14 Claims, No Drawings

WATER-SOLUBLE PRODRUGS OF PROPOFOL FOR TREATMENT OF MIGRANE

BACKGROUND OF THE INVENTION

This invention relates to the field of pharmaceuticals. More specifically, this invention relates to prodrugs of propofol that are water soluble and non-toxic.

Propofol (2,6-diisopropylphenol) is a low molecular weight phenol that is widely used as an intravenous sedative-hypnotic agent in the induction and maintenance of anesthesia or sedation in humans and animals. Among its advantages as an anesthetic are rapid onset of anesthesia, rapid clearance, and minimal side effects.

Propofol has a broad range of biological and medical applications. For example, it has been reported to be an anti-emetic (Castano et al., Rev. Esp. Anestesiol. Reanim. 42(7):257–60 (1995)), an anti-epileptic (Kuisma M. et al. Epilepsia 36(12):1241–1243 (1995)) and an anti-pruritic. (Borgeat, A. et al., Anesthesiology 80:642–56 (1994); Lawson, S. et al., Brit. J. Anesthesia 64:59–63 (1990).)

Migraine has been a well known medical problem for many years and represents one of the most investigated types of head pain. Epidemiological research has shown that in the United States, 18% of women and 6% of men suffer from migraine headaches. This extrapolates to approximately 18 million females and 5.6 million males over the age of 12 with this disorder. The prevalence of migraine, according to the Center for Disease Control, has increased 60% from 1981 to 1989. While migraine can occur at any age, 30% of migraine sufferers report their first attack before the age of ten, and the condition is most common in adolescents and young adults. The economic impact of migraine is staggering, with annual cost of the disease estimated at 18 billion dollars.

In 1938, Graham and Wolff developed the vascular hypothesis of migraine. They suggested that contraction of the intracranial arteries caused a reduction in blood flow to the visual cortex in the occipital lobe, resulting in the focal neurological symptoms ("aura") that accompany a migraine episode. As a consequence, the head pain that followed was the result of extra-cranial vasodilatation of the external carotid system, along with nerve compression in the carotid artery wall. These conclusions were based on the observation that the vasoconstricting drug ergotamine tartrate dampened pulsation of the superficial temporal artery (an end branch of the external carotid artery), resulting in migraine pain relief.

Despite the fact that the vascular model has been a dominant concept in migraine pathophysiology, several difficulties arising from this theory have been noted. These include the fact that during a common migraine attack, only minor changes in cerebral blood flow have been noted. Furthermore, oligemia, a phase of reduced blood flow, lasts for several hours longer than the aura. Lastly, the reduced blood flow is not sufficient to induce ischemia, alter neuronal function, and produce the aura phase. As a consequence of these criticisms, the central theory of migraine has been proposed.

The central theory suggests that spreading oligemia is the consequence of spreading neuronal depression, which begins as a result of decreased neuronal function in the occipital poles of the brain and progresses forward at a rate of two to three millimeters per minute. The spreading depression involves the depolarization of neurons and has associated with it marked cellular ionic abnormalities. The resulting lowered levels of cellular magnesium increase the likelihood of this type of spreading neuronal depression occurring. This repression of neural function results in a spreading oligemia that can last up to four to six hours. It progresses anteriorly, in a wave-like fashion, over the areas perfused by the middle and posterior cerebral arteries, temporarily impairing cortical vascular functioning. As a result, the aura of migraine may be the result of spreading depression, "a phenomenon originating within brain neurons and involving cerebral blood vessels only secondarily."

Many researchers have felt that serotonin (i.e., 5-hydroxytryptamine, "5HT") is the specific neurochemical cause of migraine. Platelets contain all of the 5HT normally present in blood, and after they aggregate, 5HT is released, resulting in a potent vasoconstricting effect. During a migraine attack, platelet 5HT increases in the aura phase and diminishes in the headache phase. Following a migraine attack, there is an increase in urinary 5-hydroxyindolacetic acid (5-HIAA), the main metabolite of serotonin.

While the concept of spreading neuronal depression and oligemia may explain the migraine aura, it does not account for the ensuing headache. Migraine head pain may be the result of inflammation in the trigeminovascular system (TVS). This theory suggests that the trigeminal nerve fibers innervating cranial vessels are an important component of an elaborate defense network protecting the brain from an actual or perceived insult. Inflammatory neurotransmitters such as substance P, calcitonin gene-related peptide and neurokinin A are released by the fifth cranial nerve. This release signals adjacent meningeal blood vessels to dilate. The resulting neurogenic inflammation sensitizes the neurons and this induces head pain.

A recent report has disclosed that propofol is highly effective at alleviating migraine symptoms (Krusz et al. Headache 40: 224–230 (2000)). A limiting disadvantage of propofol is that it is almost completely insoluble in water. Therefore, before it can be used for intravenous applications, such as treating migraine, it must be specially formulated in aqueous media using solubilizers or emulsifiers. The early developmental studies with intravenous propofol were performed with clear formulations containing the solubilizer Cremophor EL®. Later developmental studies and the current commercial products use an oil-in-water emulsion in which the emulsifier is the lecithin mixture Intralipid®. The commercial products are sold under various names including Diprivan®, Disoprofol®, Disoprivan®, and Rapinovet®.

Formulations that contain solubilizers or emulsifiers have been fraught with problems. Formulations containing the solubilizer Cremophor EL® have been reported to cause allergic complications (Briggs et al., Anesthesis 37:1099 (1982)). Stable emulsions are technically difficult to prepare and are consequently more expensive. Microbial growth has sometimes been observed in such emulsions and is believed to be supported by the emulsifier components (McHugh et al., Can. J. Anaesth. 42(9):801–4 (1995)). Moreover, currently available commercial formulations contain approximately 1% propofol, necessitating a large volume of administration.

Other investigators have sought to overcome the problem of water insolubility by incorporating the propofol within a water-soluble carrier such as a cyclodextrin. Such a molecular complex allows delivery of propofol in a clear water solution and the eventual release of propofol in vivo. Unfortunately, the cyclodextrin complex produced cardiovascular complications in vivo, discouraging further study (Bielen et al., Anesth. Analg. 82(5):920–4 (1996)).

Patients undergoing surgery who are anesthetized using presently available propofol formulations will likely be treated with these formulations very rarely, and most likely only once or twice during their lifetime. Thus, although current propofol preparations used for anesthesia are associated with measurable risk and other undesirable characteristics, the rarity of their repeated administration to a particular individual ameliorates, to a degree, the undesirability of these formulations. The presently used formulations are, however, inappropriate for the continued, intermittent administration necessary for the treatment and prophylaxis of migraine headaches. Thus, in view of the efficacy of propofol in the treatment of migraine, it would be highly desirable to provide to migraine sufferers a treatment method utilizing a water-soluble formulation, which is free from the difficulties associated with present oil and water emulsions of propofol.

A published PCT application naming the present inventor discloses water-soluble prodrugs and pharmaceutical preparations of propofol prodrugs, which are formulated to deliver the beneficial effects of propofol without harmful side effects arising from earlier formulations (see, WO 99/58555). The water-soluble prodrugs of propofol, such as those disclosed in the above-referenced PCT application, are useful in methods of treating or preventing migraine in subjects suffering from or prone to this condition.

SUMMARY OF THE INVENTION

For the first time, the present invention provides methods for treating or preventing migraine headaches using prodrug esters of propofol (2,6-diisopropylphenol) that are highly soluble in water and that metabolize rapidly into propofol. More specifically, this invention provides a method for treating or preventing migraine headaches by treating a subject with one or more of propofol hemisuccinate, propofol hemiglutarate, propofol hemiadipate, mono(propofol) phosphate, and di(propofol) phosphate effective to treat or prevent the migraine. The present invention provides advantages over earlier treatment methods, because the propofol esters of the present invention are at least one order of magnitude more soluble in water than propofol itself. Thus, the present invention allows the treatment of migraine headaches with a water-soluble formulation that is not hampered by the toxicity or other problems associated with earlier emulsion-based formulations The water-soluble propofol compositions offer advantages over propofol. First, the esters of propofol of this invention readily hydrolyze to propofol in vivo. Accordingly, they are useful as prodrugs of propofol. Second, they are non-toxic. Accordingly, they have a high therapeutic-to-toxicity index. Third, they have a much higher water-solubility than propofol. Thus, they offer a safer means of administration than the currently available oil-in-water or cyclodextrin formulations. Fourth, they are more stable to oxidation than propofol because they protect the phenolic function from oxidation during formulation and storage. Phenols are well known to darken and decompose in the presence of air. Therefore, the esters of propofol of this invention offer all the therapeutic effects of propofol while avoiding the necessity of adding potentially harmful solubilizing or emulsifying agents to formulations incorporating propofol.

A soluble prodrug facilitates formulation and administration of the drug. How fast the drug is released in vivo by hydrolysis is a function of the structure of the prodrug; but it is also influenced by the carrier, the route of administration, and the tissues in which the prodrug is located.

In one aspect this invention provides a method of treating or preventing migraine in a subject, the method comprising administering to the subject an amount of a propofol prodrug of the formula:

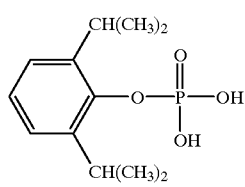

Mono(propofol) phosphate (1)

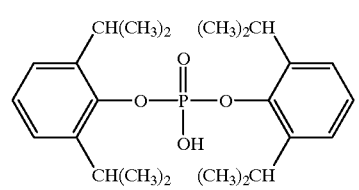

Di(propofol) phosphate (2)
or

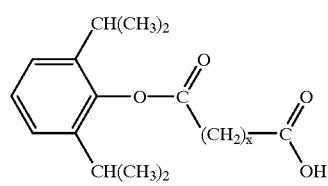

Carboxylic hemiesters of propofol (3)

effective to treat or prevent the migraine in the subject. In the formulas above, X is 2, 3 or 4. The method can also be practiced using a pharmaceutically acceptable salt of any of the foregoing.

Other objects and advantages of the present invention will be apparent to those of skill in the art from reviewing the detailed description that follows.

DETAILED DESCRIPTION OF THE INVENTION AND THE PREFERRED EMBODIMENTS

I. Water Soluble Esters of Propofol

Propofol is rendered water soluble by the linking of hydrophilic groups to the molecule. Such covalent derivatization of propofol is possible only on the phenolic —OH group, which is flanked on both sides by bulky isopropyl groups. The —OH group is therefore spatially crowded ("sterically hindered") and would be expected to be resistant to the substitution of the hydrogen with a bulkier substituent such as an acyl group or a phosphoryl group.

The synthesis of esters was successfully achieved by the use of activated diacids (as halides or anhydrides), and by simultaneous use of either catalysis by tertiary amines, or activation of the phenol by ionization of the phenolic proton.

Preferred compounds in accordance with the present invention are those having the following formulae:

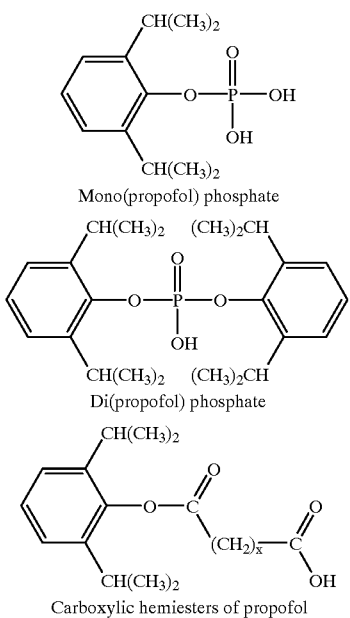

Mono(propofol) phosphate

Di(propofol) phosphate

Carboxylic hemiesters of propofol

In the above structure for carboxylic hemiesters of propofol, when X=2, this structure represents the hemisuccinate ester of propofol; when X=3, this structure represents the hemiglutarate ester of propofol; and when X=4, this structure represents the hemiadipate ester of propofol.

Preferred compounds of the present invention also include pharmaceutically acceptable salts of the compounds of the above formulae. A "pharmaceutically acceptable salt" is a salt that can be formulated into a composition for pharmaceutical use including, e.g., metal salts (sodium, potassium, magnesium, calcium, etc.) and salts of ammonia or organic amines.

II. Prophylactic and Therapeutic Treatments

Propofol and the prodrugs described herein are useful for the prophylactic and therapeutic treatment of migraine in "subjects" as described herein. A "subject" of treatment is an animal, preferably a human. "Treatment" refers to prophylactic or therapeutic treatment. A "prophylactic" treatment is a treatment administered to a subject who does not exhibit symptoms of migraine or exhibits only early signs for the purpose of decreasing the risk of developing migraine. A "therapeutic" treatment is a treatment administered to a subject who exhibits symptoms of migraine for the purpose of diminishing or eliminating those symptoms.

III. Use as an Anti-Migraine Agent

Propofol and its prodrugs, as described herein, are useful in methods of treating and/or preventing migraine in subjects. The methods involve administering to the subject an amount of a prodrug of the invention effective to treat or prevent the migraine. In the therapeutic methods of this invention, a pharmacologically effective amount of the compound is administered to a subject suffering from a migraine headache. In the prophylactic methods of this invention a pharmaceutically effective amount of the compound is administered to a subject at risk of developing a migraine.

IV. Pharmaceutical Compositions and Modes of Delivery

Propofol and the prodrugs of this invention preferably are delivered as pharmaceutical compositions. "Pharmaceutical composition" refers to a composition suitable for pharmaceutical use in a subject. The pharmaceutical compositions of this invention comprise a pharmacologically effective amount of a compound of the invention and a pharmaceutically acceptable carrier. "Pharmacologically effective amount" refers to that amount of the compound effective to produce the intended pharmacological result, i.e., treat or prevent migraine. "Pharmaceutically acceptable carrier" refers to any of the standard pharmaceutical carriers, buffers, and excipients, such as a phosphate buffered saline solution, aqueous solutions of dextrose, and emulsions, such as an oil/water or water/oil emulsion, and various types of wetting agents and/or adjuvants. Suitable pharmaceutical carriers and formulations are described in *Remington's Pharmaceutical Sciences,* 19th Ed. (Mack Publishing Co., Easton, 1995). Preferred pharmaceutical carriers can be selected by those of skill in the art and generally depend upon the intended mode of administration of the active agent.

The compounds of the invention can be formulated for administration in a variety of ways. Typical routes of administration include, for example, oral, enteral and parenteral. These include, without limitation, subcutaneous, intramuscular, intravenous, intraperitoneal, intramedullary, intrapericardiac, intrabursal, oral, sublingual, ocular, nasal, topical, transdermal, transmucosal, or anal. The mode of administration can be, e.g., via swallowing, inhalation, injection or topical application to a surface (e.g., eyes, mucus membrane, skin).

Particular formulations typically are appropriate for specific modes of administration. Various contemplated formulations include, for example, aqueous solutions, solid formulations, aerosol formulations and transdermal formulations.

A. Aqueous Solutions for Enteral, Parenteral or Transmucosal Administration

Examples of aqueous solutions include, for example, water, saline, phosphate buffered saline, Hank's solution, Ringer's solution, dextrose/saline, glucose solutions and the like. The compositions can contain pharmaceutically acceptable auxiliary substances as required to approximate physiological conditions or to improve stability, appearance or ease of administration, such as buffering agents, tonicity adjusting agents, wetting agents, detergents and the like. Additives can also include additional active ingredients such as bactericidal agents, or stabilizers. For example, the solution can contain sodium acetate, sodium lactate, sodium chloride, potassium chloride, calcium chloride, sorbitan monolaurate or triethanolamine oleate. These compositions can be sterilized by conventional, well-known sterilization techniques, or can be sterile filtered. The resulting aqueous solutions can be packaged for use as is, or lyophilized, the lyophilized preparation being combined with a sterile aqueous solution prior to administration.

Aqueous solutions are appropriate for injection and, in particular, for intravenous injection. Intravenous injection is a particularly appropriate means of delivery for using the compound as an antimigraine agent. The intravenous solution can include detergents and emulsifiers such as lipids. Aqueous solutions also are useful for oral and enteral and other routes of administration as tonics and administration to mucous or other membranes as, e.g., nose or eye drops. The composition can contain the compound in an amount of about 1 mg/ml to 100 mg/ml, more preferably about 10 mg/ml.

B. Solid and Other Non-aqueous Compositions for Enteral or Transdermal Delivery

Solid compositions are appropriate for oral and enteral administration. They can be formulated in the form of, e.g., pills, tablets, powders or capsules. For solid compositions, conventional nontoxic solid carriers can be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10%–95% of active ingredient.

The carrier can be selected from various oils including those of petroleum, animal, vegetable or synthetic origin, for example, peanut oil, soybean oil, mineral oil, sesame oil, and the like. Suitable pharmaceutical excipients include starch, cellulose, talc, glucose, lactose, sucrose, gelatin, maltose, rice, flour, chalk, silica gel, magnesium stearate, sodium stearate, glycerol monostearate, sodium chloride, dried skim milk, glycerol, propylene glycol, water, ethanol, and the like.

A unit dosage form, such as a tablet, can have from about 10 mg to about 3 g, preferably from about 100 mg to about 2 g of the compound.

Solid compositions are a presently preferred means of administering propofol prodrugs as antimigraine agents.

C. Topical Administration for Transdermal or Transmucosal Delivery

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents can be used to facilitate permeation. Transmucosal administration can be through nasal sprays, for example, or using suppositories.

For topical administration, the agents are formulated into ointments, creams, salves, powders and gels. In one embodiment, the transdermal delivery agent can be DMSO. Transdermal delivery systems can include, e.g., patches.

D. Delivery by Inhalation

For inhalation, the compound is preferably administered in the form of an aerosol, liquid or solid. For aerosol administration, the compound preferably is supplied in finely divided form along with a surfactant and propellant. A surfactant may be required if the agent is immiscible in the propellant.

The surfactant preferably is soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol, and the polyoxyethylene and polyoxypropylene derivatives of these esters. Mixed esters, such as mixed or natural glycerides, can be employed. The surfactant can constitute 0.1%–20% by weight of the composition, preferably 0.25%–5%.

The balance of the composition is ordinarily propellant. Liquefied propellants are typically gases at ambient conditions, and are condensed under pressure. Among suitable liquefied propellants are the lower alkanes containing up to 5 carbons, such as butane and propane; and preferably fluorinated or fluorochlorinated alkanes. Mixtures of the above can also be employed. In producing the aerosol, a container equipped with a suitable valve is filled with the appropriate propellant, containing the agent as a solution or as finely divided particles and surfactant. The ingredients are thus maintained at an elevated pressure until released by action of the valve.

A nebulizer or aerosolizer device for administering compounds typically delivers a dose of about concentration of between about 1 and 50 mg per inhalation.

Delivery by inhalation is particularly effective for delivery to respiratory tissues for the treatment of migraine. Delivery of large doses by inhalation also can induce sedation or anaesthesia. Alleviation of migraine or migraine symptoms at doses from about 20 mg to about 400 mg inhaled over a period of a few minutes (e.g., about 5 to about 15 minutes). Relief from migraine or migraine symptoms may be maintained thereafter at a dose of from about 20 mg to about 400 mg per hour for as long as is needed.

E. Other Formulations

In preparing pharmaceutical compositions of the present invention, it can be desirable to modify the complexes of the present invention to alter their pharmacokinetics and biodistribution. For a general discussion of pharmacokinetics, See, *Remington's Pharmaceutical Sciences, supra*, Chapters 37–39. A number of methods for altering pharmacokinetics and biodistribution are known to one of ordinary skill in the art. Examples of such methods include protection of the complexes in vesicles composed of substances such as proteins, lipids (for example, liposomes), carbohydrates, or synthetic polymers.

F. Administration

Single or multiple administrations of the compositions can be carried out with dose levels and pattern being selected by the treating physician. In any event, the pharmaceutical formulations should provide a quantity of a compound sufficient to treat the patient effectively.

The total effective amount of a compound of the present invention can be administered to a subject as a single dose, either as a bolus or by infusion over a relatively short period of time, or can be administered using a fractionated treatment protocol, in which the multiple doses are administered over a more prolonged period of time. One skilled in the art would know that the concentration of a compound of the present invention required to obtain an effective dose in a subject depends on many factors including the age and general health of the subject, the route of administration, the number of treatments to be administered and the judgment of the prescribing physician. In view of these factors, the skilled artisan would adjust the dose so as to provide an effective dose for a particular use.

The following examples are offered by way of illustration, not by way of limitation.

EXAMPLES

Example 1

Synthesis of Propofol Hemisuccinate

Succinic anhydride (14 g, 140 mmol) and dimethylaminopyridine (0.02 g, 0.16 mmol) were added to a solution of 2,6-diisopropylphenol (20.8 ml, 112 mmol) in triethylamine (50 ml) under nitrogen. After 16 hr at room temperature, solvents were removed under vacuum. The residue was dissolved in water and added to an iced solution of dilute hydrochloric acid. The precipitated product was filtered and recrystallized from ethanol-water to yield 25.0 g (80.2% yield) of 2,6-diisopropylphenyl hydrogen succinate (propofol hemisuccinate), mp 101–102° C.

High resolution nuclear magnetic resonance spectra are filly consistent with structure:

$^1$H-NMR (500 MHz, CDCl$_3$) δ L 1.207(d, 12H, J=6.9 Hz, di-I—Pr), 2.856(t, 2H, J=6.7 Hz, C3'—H$_2$), 2.940(q, 2H, J=6–9 HZ, C$_7$—H, C$_8$—H), 2.961 (t, 2H, J=6,7 Hz, C$_{2'}$—H$_2$), 7.173(d, 2H, J=7.8 HZ, C$_3$—H, C$_5$—H), 7.224(d, 1H, J=7.8 Hz, C$_4$—H) $^{31}$P-NMR (500 Mhz, CDCl$_3$) δ: –9.6994 $^{13}$C-NMR (500 MHZ, CDCl$_3$) δ: 22.929(C-3'), 23.916(C-

2'), 27.639(C-9, C-10, C-11, C-12), 28.815(CO7), 29.085 (C-8), 124.122(C-3, C-5), 126.805(C-4), 140.456(C-2, C-6), 145.633(C-1), 171,000(C-1'), 178.838(C-4')

Example 2

Synthesis of Propofol Hemiadipate

Triethylamine (6.26 ml, 45 mmol) and 4-dimethylaminopyridine (50 mg, 0.4 mmol) in methylene chloride (30 ml) were added to a solution of 2,6-diisopropylphenol (5.2 ml, 28 mmol) and adipoyl chloride (4.4 ml, 30 mmol) in methylene chloride (50) at 0° C. The mixture was allowed to reach room temperature and stirred at that temperature for 2 hr. Water (50 ml) was added, and the two-phase mixture was stirred for 1 hr. The organic phase was washed with 3% aqueous HCl and then dried. Solvents were removed under vacuum, and the oily residue was chromatogrammed on a silica gel column using chloroform-methanol (10:0.1) and then chloroform-methanol-acetic acid (10:0.1:0.01). The fractions containing the ester were pooled and evaporated under vacuum to yield 3.4 g (40% yield) of 2,6-diisopropylphenol hydrogen adipate (propofol hemiadipate) as an oil.

The $^1$H-NMR and $^{13}$C-NMR spectra were very similar to those of the hemisuccinate ester (example 1) and fully consistent with structure. Splitting of signals however show that the compound exists as a mixture of rotamers, most likely the result of hindered rotation about the acyl-phenoxyl linkage.

Example 3

Synthesis of Propofol Hemisuccinate Sodium Salt

A solution of propofol hemisuccinate (1.0 g, 3.6 mmol) in 10 ml of ethanol was neutralized with 3.6 ml of 1.0 N NaOH. The solvents were removed under vacuum, and water was fully removed by further addition and evaporation of acetonitrile under vacuum. The crystalline product was washed with acetonitrile and dried under high vacuum at 60° C. The yield of propofol hemisuccinate sodium salt was 0.97 g (90%).

The high resolution proton magnetic resonance spectrum and fast atom bombardment mass spectrum are fully consistent with structure:

$^1$H-NMR (500 MHz, D$_2$O) δ: 1.13(d, 12H, J=6.8 Hz, di-i-Pr), 2.622(t, 2H, J=6.7 Hz, C$_3$'—H2), 2.919(q, 2H, J=6.8 Hz, C$_7$—H, C$_8$—H), 2.937(t, 2H, J=6.7 Hz, C$_{2'}$—H2), 7.275(m, 3H, C$_3$—H, C$_4$—H, C$_5$—H)

FAB-MS: [M+H]$^+$301.1410 M/Z, calculated for C$_{16}$H$_{21}$O$_4$Na+H formula 301.1417

Example 4

Synthesis of Mono(Propofol) Phosphate Disodium Salt

Butyllithium (2.24 ml of 2.5 M solution in hexanes; 5.6 mmol) was added dropwise to propofol (1.0 g, 5–6 mmol) in 10 ml of ether at −30° C. under nitrogen. The solution was stirred at −30° C. for 30 in then allowed to warm to room temperature. This solution was then added dropwise to a solution of phosphorus oxychloride (0.918 g, 6.0 mmol) in 10 ml of ether at −30° C. The solution was allowed to warm to room temperature, then water (5 ml) was added and stirring was continued for 1 hr. Sodium hydroxide (35 ml of 1 M) and 30 ml of hexanes was added. The aqueous phase was washed with hexanes, then acidified with HCl to pH 3 and extracted with ether. After evaporation of the solvents, the oily residue was dissolved in ethanol and neutralized to pH 7.4 with 1 M NaOH. After removal of the solvents in vacuo, the residue was suspended in acetonitrile, and the solid product was collected and dried. The yield of mono (propofol) phosphate disodium salt was 1.1 g (65%).

The high resolution nuclear magnetic resonance spectra (proton, carbon and phosphorus) in water, and the fast atom bombardment mass spectrum are fully consistent with structure. The magnetic resonance spectra show the presence of two rotamers in a population ratio of 7:1:

$^1$H-NMR (500 MHz, D$_2$O) δ: 1.184 and 1.205 (d,d, 12H, J=6.8 Hz, di-i-Pr), 3.519 and 3.619 (m,m, 2H, C$_7$—H, C$_8$—H), 7.198 (m, 3H, C$_3$—H, C$_4$—H, C$_5$—H) $^{13}$C-NMR (500 MHz, D$_2$O) δ: 21.986 and 22.083 (C-9, C-10, C-11, C-12), 22.212 and 25.826 (C-7, C-8), 123.212 (C-3, C-5), 140.922 and 140.992 (C-2, C-6), 146.244, 146.315 and 146.502 (C-1) 3'P-NMR (500 MHz, D$_2$O) δ: −3.735 and −15.223

FAB-MS: [M+H]$^+$303.0730 M/Z, calculated for C$_{12}$H$_{17}$O$_4$PNa+H formula 303.0739

Example 5

Synthesis of Di(Propofol) Phosphoric Acid Ester

Butyllithium (2.24 ml of 2.5M solution in hexanes; 5.6 mmol) was added dropwise to propofol (1.0 g, 5.6 mmol) in 10 ml of ether at −30° C. under nitrogen. The solute on was stirred at −30° C. for 30 min then allowed to warm to room temperature. To this solution was then added dropwise a solution of phosphorus oxychloride (0.444 g, 2.9 mmol) in 5 ml of ether at −30° C. The solution was allowed to warm to room temperature, then water (5 ml) was added and stirring was continued for 1 hr. Sodium hydroxide (20 ml of 1 M) and 20 ml of hexanes was added. The organic phase was washed with 1 M NaOH, water, then dried over sodium sulfate. The solvents were removed and the residue was dissolved in acetone (10 ml) and treated with 10 ml of 1 M NaOH and stirred for 2 hr. Most of the acetone was removed and the aqueous residue was adjusted to pH 5 with HCl, followed by extraction with hexanes. Evaporation of the hexanes left a white crystalline solid of di(propofol) phosphoric acid ester. The yield was 0.920 g (75%), mp 154° C.

The nuclear magnetic resonance spectra (proton and phosphorus) were consistent with structure:

$^1$H-NMR (500 MHz, CDCl$_3$) δ: 1.036(d, 24H, J=6.6 Hz, tetra-i-Pr), 3.342(m, 4H, J=6.6 Hz, C$_7$—H, C$_8$—H, C$_{7'}$—H, C$_{8'}$—H), 7.047 (d, 4H, J=7.5 Hz, C$_3$—H, C$_5$—H, C$_{3'}$—H, C$_{5'}$—H), 10.400 (broad, 1H, P-OH) $^{31}$P-NMR (500 MHz, CDCl$_3$) δ: −9.6994

Example 6

Synthesis of Di(propofol) Phosphate Monosodium Salt

A solution of di(propofol) phosphoric acid ester (300 mg, 0.7 mmol) in 5 ml of ethanol was neutralized to pH 7.4 with 0.7 ml of 1 M NaOH. After removal of the solvent under vacuum, the residue was dissolved in ether and again evaporated to yield di(propofol) phosphate disodium salt as a white solid, 300 mg, 100% yield.

The fast atom bombardment mass spectrum was consistent with structure:

FAB-MS: [M+H]$^+$436.1977 M/Z, calculated for $C_{24}H_{34}O_4PNa+Na$ formula 436.1979

Example 7

In Vitro Hydrolysis of Propofol Esters in Various Media

General procedure: Propofol ester was dissolved in the test medium at room temperature, and samples were removed periodically for analysis. The samples were extracted with hexane, the extracts were evaporated to dryness, and the residues were taken up in methanol. Analysis was by HPLC using methanol solvent through an ODS column and UV detection at 260 nm.

The approximate half-life for the hydrolysis of propofol hemisuccinate to propofol in various media were as follows:

| Medium | Half-Life to Hydrolysis |
| --- | --- |
| water (PBS buffer pH 7.4) | 2 weeks |
| albumin | 6 days |
| human saliva | 4 days |
| human plasma | 3 days |
| human blood, whole | 2 days |
| rat blood, whole | 2 hrs |

The approximate half-life for the hydrolysis of (mono) propofol phosphate to propofol in human saliva was about four days.

Example 8

In Vivo Hydrolysis of Propofol Hemisuccinate

Propofol hemisuccinate sodium salt in aqueous solution was administered to adult male Sprague-Dawley rats by gavage. Blood was collected at 2, 4, 8 and 24 hours after dosing, and analyzed by HPLC as described in example 3. Peak blood levels of propofol were seen at 2 to 4 hrs after dosing. At a dosage of 400 mg of propofol hemisuccinate per kg body weight, the blood level of propofol at 4 hrs was about 1 $\mu$g/ml. All the animals remained healthy and active through the two day observation period following the dosing.

Example 9

Effect of Propofol Esters on LDL-oxidation by Copper, and by Hydrogen Peroxide/Horseradish Peroxidase The following experiment is based on the use of low density lipoprotein (LDL) as an oxidizable substrate. LDL is one of the plasma lipoproteins whose oxidation is thought to contribute to the pathogenesis of atherosclerosis. The copper-promoted, the hydrogen peroxide-/horseradish peroxidase-promoted and the myeloperoxidase-promoted oxidation of LDL are models for the free radical-induced oxidation of LDL that occurs in vivo.

LDL was isolated from heparinized plasma of normal human donors by ultracentrifugation. Most of the experiments described in this study were performed immediately after isolation. Examples and further details of the experimental procedures may be found in N. Santanam et al *J. Clin Invest.* 95(6):2594 (1995) and *FEBS Letters,* 414:549–551 (1997).

The formation of conjugated dienes was measured in a spectrophotometer (model DB-3500; SLM-AMINCO, Urbana, Ill.) equipped with a 12 position sample changer. Samples and references were measured continuously for periods of up to several hours. Typically, 100 $\mu$g/ml of LDL was incubated in PBS with 1 U horseradish peroxidase (type X, 260 U/mg) in the presence of 50 $\mu$M $H_2O_2$. For copper-mediated oxidation, 100 $\mu$g/ml LDL was incubated with 5 $\mu$M copper sulfate solution.

The copper-promoted oxidation of LDL was not significantly affected by the presence of the propofol prodrugs (propofol phosphate, dipropofol phosphate, propofol hemisuccinate) at concentrations of 5 $\mu$M. However, in the presence of 5 $\mu$M propofol, the oxidation was almost totally inhibited.

The oxidation of LDL in the presence of horseradish peroxidase/hydrogen peroxide was not significantly affected by the presence of either di(propofol)phosphate (5 $\mu$M) or propofol monophosphate (5 $\mu$M). In the presence of propofol hemisuccinate (5 $\mu$M) the oxidation was slightly inhibited. In the presence of 5 $\mu$M propofol, the oxidation was almost totally inhibited.

The oxidation of LDL in the presence of myeloperoxidase was partly inhibited in the presence of propofol hemisuccinate.

Example 10

Effect of Propofol Esters on LDL-oxidation by Copper, and by Hydrogen Peroxide/Horseradish Peroxidase Human low density lipoprotein (huLDL) in the presence of myeloperoxidase undergoes oxidative modification. The oxidative damage may be measured by spectrophotometric detection of the resulting conjugated dienes (N. Santanam & S. Parthasarathy, *J. Clin. Invest,* 95(6):2594 (1995)). Following the procedures of Santanam et al., it was observed that the myeloperoxidase-mediated oxidation of huLDL was significantly inhibited in the presence of added propofol hemisuccinate.

The present invention provides water soluble esters of 2,6-diisopropylphenol and methods of using these compounds. While specific examples have been provided, the above description is illustrative and not restrictive. Many variations of the invention will become apparent to those skilled in the art upon review of this specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted. Applicants do not admit by their citation of various references in this document that any particular reference is "prior art" to their invention.

What is claimed is:

1. A method of treating or preventing migraine in a subject, said method comprising, administering to said subject a prodrug of propofol of the formula:

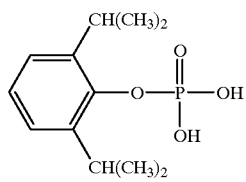

Mono(propofol) phosphate

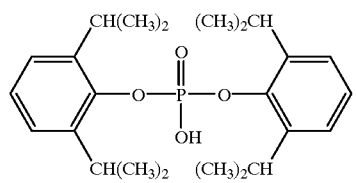

Di(propofol) phosphate
or

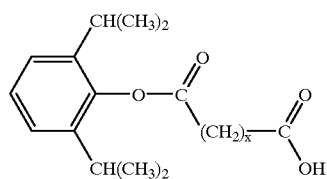

Carboxylic hemiesters of propofol wherein X is 2, 3 or 4, or a pharmaceutically acceptable salt of any of the foregoing in an amount effective to treat or prevent said migraine.

2. The method according to claim 1, wherein said prodrug is a component of a pharmaceutical composition comprising a pharmaceutically acceptable carrier and a pharmacologically effective amount of said prodrug or a pharmaceutically acceptable salt thereof.

3. The method of claim 2 wherein the pharmaceutically acceptable carrier is an aqueous solution.

4. The method of claim 2 wherein the pharmaceutically acceptable carrier comprises a transdermal delivery vehicle.

5. The method of claim 2 wherein said composition is an injectable solution.

6. The method of claim 2 wherein said composition is contained in an aerosolizer or inhaler.

7. The method of claim 2 wherein said composition is contained in a transdermal delivery system.

8. The method according to claim 2 wherein said composition is in a unit dosage form.

9. The method of claim 2 wherein the pharmaceutically acceptable carrier contains a detergent, an emulsifier or liposomes.

10. The method of claim 5 wherein the concentration of the compound in the injectable solution is between about 1 mg/ml to about 100 mg/ml.

11. The method of claim 8 wherein the unit dosage form contains about 10 mg to about 3 gm of the compound.

12. The method of claim 11 wherein the unit dosage form contains about 100 mg to about 1 gm of the compound.

13. The method of claim 2, wherein said composition further comprises a second antimigraine agent.

14. The method of claim 12 wherein said second antimigraine agent is a member selected from analgesics, triptans, dihydroergotamine, opiates, antiinflammatories and combinations thereof.

* * * * *